United States Patent [19]

Stewart

[11] Patent Number: 4,473,693

[45] Date of Patent: Sep. 25, 1984

[54] AMINONAPHTHALIMIDE DYES FOR INTRACELLULAR LABELLING

[76] Inventor: Walter W. Stewart, Bldg. 4, Room 307, National Institutes of Health, Bethesda, Md. 20014

[21] Appl. No.: 931,273

[22] Filed: Aug. 4, 1978

[51] Int. Cl.$^2$ .................. C07D 221/14; G01N 33/16; G01N 1/30
[52] U.S. Cl. ...................................... 546/100; 424/3; 424/7.1
[58] Field of Search ...................... 260/281 S; 424/3; 546/100

[56] References Cited

U.S. PATENT DOCUMENTS

| | | | |
|---|---|---|---|
| 1,796,011 | 3/1931 | Eckert | 260/281 |
| 1,836,529 | 12/1931 | Eckert | 260/281 |
| 1,984,110 | 12/1934 | Bodmer | 260/281 |
| 2,096,295 | 10/1937 | Eckert | 260/281 |
| 2,455,095 | 11/1948 | Scalera | 260/281 |
| 3,147,264 | 9/1964 | Klein | 260/281 |
| 3,340,225 | 9/1967 | Dressler | 260/45.8 |
| 4,051,134 | 9/1977 | Friedvich et al. | 260/281 |
| 4,055,565 | 10/1977 | Hotta | 260/281 |

FOREIGN PATENT DOCUMENTS

| | | |
|---|---|---|
| 494446 | 3/1930 | Fed. Rep. of Germany . |
| 515029 | 12/1930 | Fed. Rep. of Germany . |
| 589556 | 11/1933 | Fed. Rep. of Germany . |
| 44-15296 | 7/1969 | Japan . |
| 299721 | 1/1930 | United Kingdom . |
| 304739 | 4/1930 | United Kingdom . |
| 384901 | 1/1933 | United Kingdom . |

OTHER PUBLICATIONS

Stewart et al., *Nature*, 292, 17–21 (1981).
Colour Index, 3rd Edition, vol. 4, p. 4508.

*Primary Examiner*—Mark L. Berch
*Attorney, Agent, or Firm*—John S. Roberts, Jr.

[57] ABSTRACT

Fluorescent yellow dyes of the aminonaphthalimide type which have the following structures:

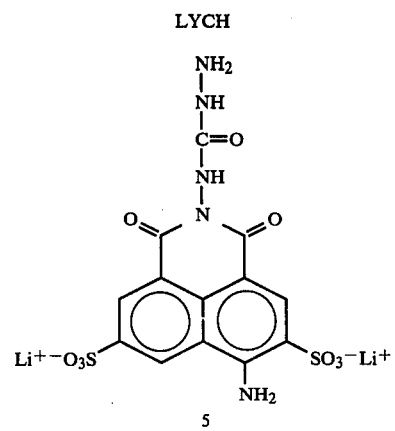

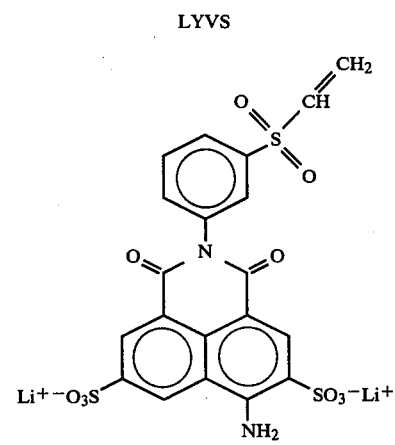

In the formula above alk (alkali metal) may be substituted for Li$^+$ and thus alk may be Li$^+$, Na$^+$, or K$^+$, but the preferable structure is Li$^+$. These dyes have shown superior activity in intracellular use in vivo in tissues such as turtle retina and wholemount tissue observation.

4 Claims, No Drawings

AMINONAPHTHALIMIDE DYES FOR INTRACELLULAR LABELLING

This invention relates to fluorescent yellow dyes of the aminonaphthalimide type which have the following structures:

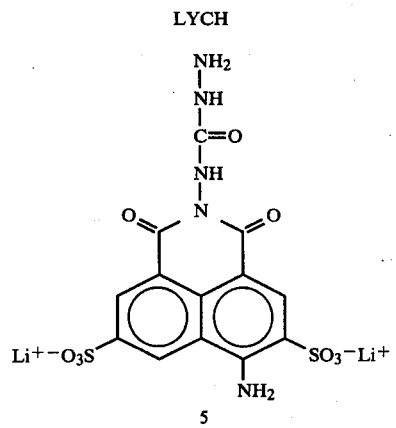

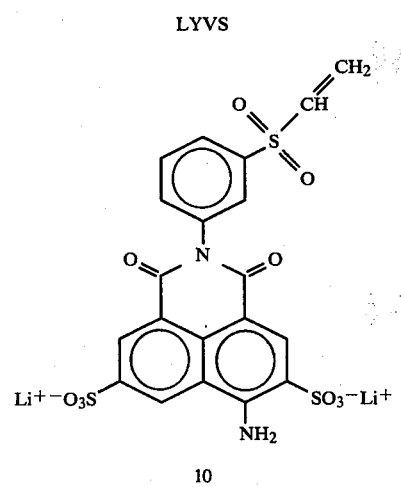

In the formula above alk (alkali metal) may be substituted for $Li^+$ and thus alk may be $Li^+$, $Na^+$, or $K^+$, but the preferable structure is $Li^+$. These dyes have shown superior activity in intracellular use in vivo in tissues such as turtle retina.

PRIOR ART STATEMENT

In *Colour Index*, Third Edition, The Society of Dyers and Colourists, Volume 4, page 4508, the dye set out as No. 56205 is the closest literature citation and is also known as Brilliant Sulfoflavin FF.

The other related dyes from the Colour Index are Nos. 56200 and 56210.

The patent references noted in the Colour Index for the above three dye numbers are as follows:

No. 56200—British Pat. No. 304,739; U.S. Pat. No. 1,836,529; German Pat. No. 515,029 (French Pat. No. 171,511);

No. 56205—British Pat. No. 299,721; U.S. Pat. No. 1,796,011; German Pat. No. 494,446 (French Pat. No. 16,850);

No. 56210—U.S. Pat. No. 1,796,011; British Pat. No. 299,721; German Pat. No. 494,446 (French Pat. No. 16,850); British Pat. No. 384,901; U.S. Pat. No. 1,984,110; German Pat. No. 589,566 (French Pat. No. 201,038).

The above-noted patent references apply to the structures given.

Additionally, the following U.S. patents are of interest:

U.S. Pat. Nos. 3,147,264; 3,340,225 Dressler et al.; and U.S. Pat. No. 4,055,565 Hotta et al.

The synthesis of the dye compounds of this invention are set out below in the flow chart.

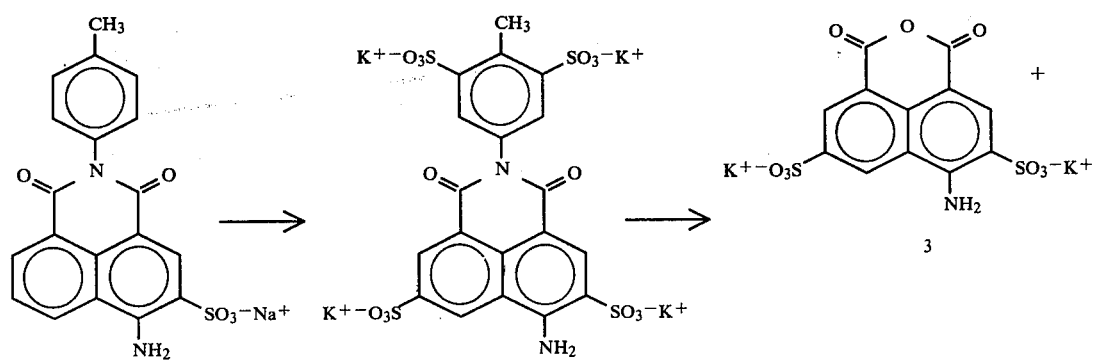

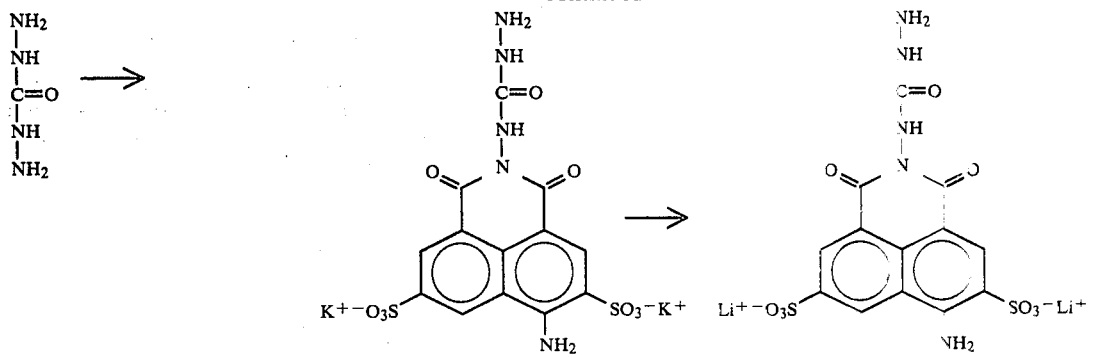

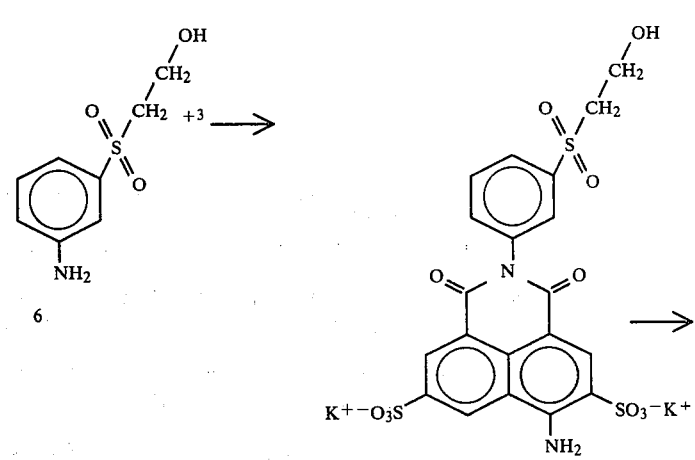

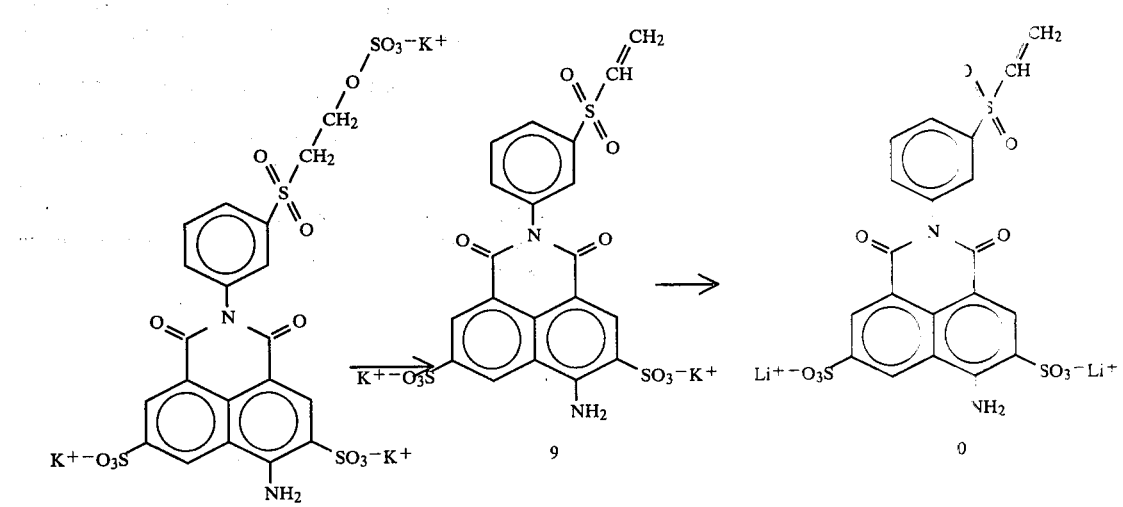

It us noted that Lucifer Yellow CH, compound 5, is a condensation product of anhydride (3) and carbohydrazide. Lucifer Yellow VS, compound 10, is a vinyl sulfone, which reacts covalently with proteins, presumably through the amino and sulfhydryl groups.

It is known that the anhydride (3) is fluorescent when reacted with amines and constitutes a key building block for the Lucifer Yellow CH compound. As to the sulfone LYVS, the fraction 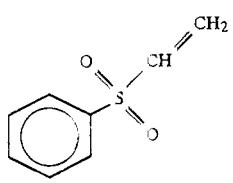 is the reactive portion.

In Table I below is shown the quantum yield of Lucifer and other dyes. Unlike most fluorescent dyes, Lucifer dyes have about the same quantum yield between pH 1 and 10. A quantum yield is a ratio of photons emitted to photons absorbed and a perfect fluorescer has a quantum yield of 1.0. Both Lucifer dyes have quantum yields of 0.2.

The competing dye in the table, Procion Yellow M-4RS, developed by Stretton and Kravitz (1969), has an uncertain structure due to the lack of a published synthesis but is a yellow tissue reactive fluorescent dye. The quantum yield of Procion Yellow is quite low with an average of $3.6 \times 10^{-4}$. Thus, from the table, the quantum yields in water of the two Lucifer dyes are about 500 times greater than the quantum yield of Procion Yellow.

TABLE I

Quantum Yield of Fluorescent Dyes

| Dye | Stimulating Wavelength nm | Emission Maximum nm | Quantum Yield |
|---|---|---|---|
| Lucifer Yellow CH | 420 | 540 | 0.21 |
| Lucifer Yellow VS | 430 | 535 | 0.24 |
| Procion Yellow M-4RS[a] | 470 | 600 | 0.00032 |
| Procion Yellow M-4RS[a] | 500 | 600 | 0.00040 |
| Fluorescein[b] | 490 | 515 | 1.0 |

[a] Because the quantum yield of Procion Yellow is very low, it was necessary to use concentrated solutions of the dye. These concentrated solutions required large corrections for self-absorption. Values for the quantum yield of Procion Yellow were determined at two different stimulating wave lengths, 470 nm and 500 nm; both values are of low accuracy.
[b] Icluded as a control.

UTILIZATION OF THE DYES

General Background

In the marking of nerve cells utilization of the present dyes is substantially more sensitive than any of those previously available and preferred is the Lucifer Yellow CH (compound 5) dye, which is a part of this invention. This dye can be viewed both in living tissue and in tissue after fixation and embedding. The intense fluorescence of the dye makes injected neurons visible in the living state as well as in cleared wholemounts where the complex three-dimensional structure of neurons is readily apparent. In marking nerve cells with the Lucifer Yellow CH, many of the invertebrate neurons studied have been found to possess an extensive and complex array of fine processes not visible with other techniques. In the turtle retina, dye was frequently observed to spread rapidly from injected cell to other cells by a movement of the dye from cell to cell, termed here "dye-coupling" which occurs primarily but not exclusively between cells known to be electrically coupled.

Historical Background

The electrical activity of single nerve cells is usually studied by means of a fine glass micropipette, which is advanced gradually into neural tissue until electrical monitoring of the micropipette indicates that its tip has penetrated a nerve cell. The electrical behavior of that cell can then be recorded, but its shape and its location relative to other nerve cells are usually unknown. Because the shape and location of nerve cells are strong clues to their function, it is desirable to mark the cell so that it can be seen.

Marking nerve cells has proved difficult. All methods depend on injecting a marker substance, usually a dye, into the cell through the micropipette. The first attempts, made during the 1950's and the early 1960's, resulted in a deposit of stain up to several hundred microns in diameter, far beyond the boundaries of the injected cell. Often the injected cell could not even be identified. Kerkut and Walker [Stain Technol., 37:217–219 (1962)] injected cells with potassium ferrocyanide, then incubated the tissue in ferric chloride to produce a precipitate of Prussian Blue which remained inside the injected cells. Behrens and Wulff [J. Gen. Physiol., 48:1081–1096 (1965)] succeeded in marking single cells with Aniline Blue and with a mixture of Fast Green FCF and Orange G. Thomas and Wilson [Science, 151:1538–39 (1966)] stained cat motoneurons with Methyl Blue and were able to observe clearly the branching of fine dendrites. Other early work has been reviewed by Nicholson and Kater [The Development of Intracellular Staining. In Intracellular Staining in Neurobiology, New York, Springer-Verlag, pages 1–19 (1973)].

These methods had two drawbacks. First, the stains were not covalently bound to the tissue; in order to minimize leakage of stain from the injected cell, the tissue had to be processed in ways which resulted in serious distortions of structure. Second, the methods were all relatively insensitive since they all depended on light absorption for detection of the marked cell. To be visible, a cell had to contain large amounts of dye. Stretton and Kravitz [Science, 162:132–134 (1969)] solved the first of these problems by introducing the tissue-reactive fluorescent dye Procion Yellow M-4RS. This dye remains in place during fixation and dehydration, presumably because it combines covalently with tissue components.

The development of Procion Yellow did not solve the second problem, the low sensitivity of earlier methods. Because of the low fluorescence efficiency, Procion Yellow is only slightly easier to detect than dyes which depend on light absorption. In comparative experiments between Procion Yellow and the present Lucifer Yellow CH, the two dyes were compared directly by injection into matched neurons in the cerebropleural ganglia of a nudibranch mollusk.

Photometric studies of the concentration of dye in sections of fixed and embedded cells show that the concentration of dye in a well marked cell is about $10^{-3}$ M and that probably Lucifer Yellow CH is visible in cells down to about $10^{-6}$ M. Therefore, the concentration of the dye in the micropipette should be at least $10^{-3}$ M, and this value is designated as a satisfactory concentration for both LYCH and LYVS. The amount of dye injected should be of a satisfactory concentration and governed by the cell volume.

It was also observed that with the Lucifer Yellow CH dye in the cell it spread within seconds through injected cells, whereas prior art dyes are thought to spread slowly after injection up to a period of several hours.

The fading rate for fluorescence intensity of Lucifer dyes varies with the intensity of illumination. For example, Lucifer Yellow CH illuminated with a 200 watt mercury lamp where the power intensity at the object plane was $1.4 \times 10^{-5}$ joules/m² sec., the half life in the first two hours was about one hour (time to half intensity). Other experiments showed a 75% loss of fluorescent intensity of 20 minutes from a cell marked Lucifer Yellow CH.

The Lucifer Yellow dyes have been shown to be relatively non-toxic by i.v. and oral administration in mice.

Electrical Coupling and Dye-Coupling

The spreading of the Lucifer dyes is related to the two effects known as electrical coupling and dye-coupling.

For almost twenty years it has been known that the cells of certain tissues are electrically coupled; that is, a voltage change imposed on a single cell will induce a voltage change in its neighbors. This induced voltage change is a consequence of the flow of current from the first to the second cell without the mediation of a chemical synapse. In 1962 Loewenstein and Kanno [J. Cell. Biol., 22:565-586 (1964)] made a related finding: they showed that in the electrically coupled cells of the salivary gland of Drosophila larvae, fluorescein injected into a single cell soon spreads to adjacent cells. Since then, in practically every electrically coupled system that has been examined, dye has been found to spread from the injected cell to the coupled cells.

All investigations of dye movement have been handicapped by the nature of the available tracers. Fluorescein, the most commonly used and the most sensitive tracer, cannot be bound to tissue by fixatives. Since the dye is lost during fixation, injected tissue must be examined alive in wholemount. But when tissue is unfixed, unsectioned, and unstained, some important features of the tissue will be misinterpreted or overlooked altogether. Furthermore, since the preparations have to be examined immediately, the experiment must be performed on the stage of a fluorescence microscope. This requirement has greatly restricted the value of the technique. Also, since fluorescein is known to pass through the intact membranes of live cells, the interpretation of dye movement is ambiguous: dye may be spreading to adjacent cells either directly or by way of the extracellular space. Procion Yellow has also been used as a tracer of intercellular connections. This dye does not penetrate cell membranes [Payton, Bennet, and Pappas, Science, 166:1641-43 (1969)] and is easily bound to tissue but is of limited value because of its low sensitivity. Dansylated amino acids [Johnson and Sheridan, Science 174: 717-719 (1971); Simpson et al., Science, 195:294-296 (1977)] are tracers of intermediate sensitivity and probably do not pass through cell membranes but are lost during fixation.

Dye-transfer studies are informative with the use of Lucifer Yellow CH, a sensitive tracer that is not lost during fixation: some patterns of coupled cells are intrinsically easier to detect with dye-coupling than with electrical coupling.

EXAMPLE 1

Preparation of Dye Lucifer Yellow CH (Compound 5)

The dyes used for intracellular injection were synthesized according to the scheme shown supra. Details of the preparative methods are as follows.

One hundred grams of commercial brilliant sulfoflavine (Brilliant Sulfoflavine FFA) (1) was dissolved in 3 liters of hot 2% KCl, treated with 10 g Nuchar CN, filtered, and allowed to cool. The crystalline residue was recrystallized from 1300 ml boiling water, collected, washed with ethanol, ether, and dried at 120° C. in vacuo to give 41.6 g minute yellow needles, a yield of 71%. NMR (D$_2$O, 98° C.): $\delta 2.38$ (s), $\delta 7.04$ (d, J = 8 Hz), $\delta 7.17$ (m), $\delta 7.93$ (d, J = 8 Hz), $\delta = 8.52$ (s). Anal. calcd for $C_{19}H_{13}KN_2O_5S$: C, 54.27; H, 3.12; N, 6.66; S, 7.63; ash, 20.72. Found, dried at 105°: C, 54.02; H, 3.20; N, 6.62. Found: C, 54.28; H, 3.35; N, 6.85; S, 7.48; ash, 20.55. UV$_{max}$ (H$_2$O) 275 nm ($\epsilon 2.06 \times 10^4$), 420 nm ($\epsilon 1.48 \times 10^4$).

Tetrasulfonate (2). One hundred g commercial brilliant sulfoflavine (1) was dissolved in 300 ml 30% fuming H$_2$SO$_4$, and held at 130° C. for 24 hours, diluted to 3 liters over ice, was treated with 10 g Nuchar CN for 10 minutes, and filtered. Three hundred grams KCl was dissolved in the filtrate at 90° C. and the resulting homogenous solution was allowed to cool to room temperature with constant stirring. Crystallization was completed by stirring for two days at 4° C. The dried product, a light yellow powder turning orange on hydration, weighed 96.49 g, a 90% yield. NMR in D$_2$O at 98°: $\delta 3.20$ (s, 3 H), $\delta 8.30$ (s, 2 H), $\delta 8.82$ (d, J = 2 Hz, 1 H), $\delta 8.93$ (d, J = 2 Hz, 1 H), $\delta 8.95$ (s, 1 H). UV$_{max}$ 278, 425 nm. Anal. calcd for $C_{19}H_{10}K_4N_2O_{14}S_4$: C, 29.45; H, 1.30; N, 3.62; S, 16.55; ash 43.97. Found, dried at 105°: C, 28.83; H, 1.61; N, 3.62. Found, equilibrated and corrected: C, 29.56; H, 1.12; N, 3.74; S, 16.27; ash, 43.81.

Anhydride (3). One hundred grams of tetrasulfonate (2) dissolved in 2 liters 3% KOH was held for 10 minutes at 50° C., then acidified with HCl to pH 2 (copious crystallization) and held at 50° C. for 10 minutes. This cycle, between pH 12.5 and pH 2, was repeated three more times. The final suspension of crystals was allowed to stir at pH 2 for 3 days at room temperature, then raised to pH 4.5 with KOH. The product dried at 80° C. in vacuo weighed 56.6 g (98% yield) and was a stable, light yellow, non-hygroscopic powder. NMR in basic solution at 98° C. showed: $\delta 8.18$ (s, 1 H), $\delta 8.20$ (d, J = 2 Hz, 1 H), $\delta 8.68$ (d, J = 2 Hz, 1 H). UV$_{max}$ in H$_2$O: 280, 418 nm. UV$_{max}$ in base: 265, 349 nm. Anal. calcd for $C_{12}H_5K_2NS_2O_9$: C, 32.06; H, 1.12; N, 3.12; S, 14.27; ash, 38.77. Found, after recrystallization from H$_2$O: C, 31.95; H, 1.18; N, 3.22; S, 13.47; ash, 37.52.

Carbohydrazide adduct (4) was prepared by boiling briefly a suspension of 44.95 g anhydride (0.1 mole) in a solution of 90 g of carbohydrazide in 1 liter H$_2$O. When the anhydride was entirely dissolved, 1 liter of 2% KCl was added and the resulting solution was cooled with stirring to room temperature. The product was recrystallized with 2.5 g Nuchar CN from 2 liters boiling 1% KCl to give 42.61 g hygroscopic yellow needles, a yield of 82%. Anal. calcd. for $C_{13}H_9K_2N_5O_9S_5$: C, 29.94; H, 1.74; N, 13.43; S, 12.29; ash, 33.40. Found, for 8.15% moisture: C, 30.76; H, 2.17; N, 13.08; S, 11.97; ash, 32.76.

The dilithium salt of the carbohydrazide adduct (5). dilithium 6-amino-2-[(hydrazino carbonyl) amino]-2,3 dihydro-1,3-dioxo-1H-benz [de]isoquinoline-5,8-disulfonate, given the name "Lucifer Yellow CH," was prepared from a solution of 15 g 4 dissolved with heating in 375 ml H$_2$O. This solution was passed over a 150 meq column of Dowex 50W × 2 50-100 mesh in the dilithium form; the column was washed with H$_2$O to remove all dye, and the pooled eluate was passed through a 0.22 μm Millipore filter and lyophilized to yield 13.07 g (99% yield) of a fluffy orange hygroscopic powder. Anal. calcd. for $C_{13}H_9Li_2N_5O_9S_2$: C, 34.15; H, 1.98; N, 15.32; S, 14.02; ash, 24.06. Found for 13.22% moisture: C, 33.83; H, 2.77; N, 14.72; S, 13.74; ash, 23.45.

EXAMPLE 2

Preparation of Dye, Lucifer Yellow VS (Compound 10)

Amino benzene 3 hydroxyethyl sulfone (6) was utilized as the starting material. Seventy-five grams of the dark red powder was recrystallized from 3 liters CHCl$_3$ with 2.5 g Nuchar CN to give 56 g of the pure material as large tan needles.

Adduct 7 was prepared by refluxing a suspension of 67.5 g of 3 in a solution of 60.4 g 6 (a two-fold molar excess) in 1 liter H$_2$O. When the suspension cleared after 42 hours, the solution was filtered, made to 1.6 liters 2% in KCl, and allowed to cool with stirring, first to room temperature, then to 4° C. The dried product weighed 71.9 g, a yield of 76%.

The sulfate compound 8 was prepared by dissolving 40 g of finely powdered 7 in 120 ml H$_2$SO$_4$ at 4° C.; complete solution required 24 hours. The sulfuric acid solution was diluted to 1.2 liters over ice, made 5% in KCl, heated to about 50° C. to dissolve the crystals, and allowed to cool to 4° C. with stirring. The product was collected, washed with 10% and 5% KCl, suspended in 1 liter H$_2$O at 4° C., and carefully neutralized with 0.1 N KOH. The suspension was heated to about 40° C. to dissolve the crystalline precipitate that formed, filtered, made 2% in KCL, and cooled with stirring, first to room temperature, then to 4° C. The product was collected, washed lightly with cold H$_2$O, and dried in vacuo to yield 42.5 g (89%) hygroscopic yellow crystals. The NMR at 98° C. in D$_2$O showed: $\delta$3.98 (t, J=6 Hz, 2 H), $\delta$4.57 (t, J=6 Hz, 2 H), $\delta$8.0 (m, 4 H), $\delta$8.68 (d, J=2 Hz, 1 H), $\delta$8.75 (d, J=2 Hz, 1 H), $\delta$8.80 (s, 1 H).

The dipotassium salt of the vinyl sulfone adduct, 9, was prepared by dissolving 15.0 g 8 (20 mmoles) in 300 ml H$_2$O, and slowly adding 1 N NaOH to maintain the pH at 10. Uptake of base stopped after 17 ml; the crystalline suspension was neutralized with HCl and set at 4° C. to complete crystallization. Dried, the product weighed 11.86 g a yield of 96%. The NMR at 98° C. in D$_2$O showed: $\delta$6.17 (s), $\delta$6.27 (s), $\delta$6.35 (s), $\delta$6.55 (s), $\delta$6.77 (s), $\delta$6.93 (s), $\delta$7.03 (s), $\delta$7.25 (s), $\delta$7.93 (s) [These signals had a combined integral of 3H], $\delta$7.9 (m, 4 H), $\delta$8.73 (s,1 H), $\delta$8.80 (d, J=2 Hz, 1 H), $\delta$8.88 (d, J=2 Hz, 1 H). The NMR was unchanged after one hour at 98° C. Anal calcd. for C$_{20}$H$_{12}$K$_2$N$_2$O$_{10}$S$_3$: C, 39.08; H, 1.97; N, 4.56; S, 15.65; ash 28.34. Found for 9.62% moisture: C, 38.95; H, 2.45; N, 4.66; S, 15.36; ash, 28.42. Found, dried at 105° C.: C, 39.06; H, 2.04; N, 4.71.

The dilithium salt 10, referred to as "Lucifer Yellow VS," was prepared by ion exchange. Ten grams 9 was dissolved with gentle heating in 300 ml H$_2$O, passed over a 100 meq column of Dowex 50W×2 50-100 mesh in the lithium form, and eluted with H$_2$O. The eluate was passed through a 0.22 um Millipore filter and lyophilized to yield 9.39 g of hygroscopic yellow powder. Theory is 8.96 g, which indicates residual hydration. Anal. calcd. for C$_{20}$H$_{12}$Li$_2$N$_2$S$_3$O$_{10}$: C, 43.64; H, 2.20; N, 5.09; S, 17.48; ash, 19.96. Found, dried at 105° C.: C, 43.36; H, 2.89; N, 5.26; S, 16.85.

EXAMPLE 3

Dye-Coupling in the Turtle Retina

In an experiment with the turtle retina, a remarkably high proportion of the cells in the turtle retina were dye-coupled to other cells. For example, of the 25 injected cells whose images could be interpreted in whole-mount, 19 were dye-coupled to other cells.

The mechanisms responsible for the observed dye-coupling are not known. It is significant that 14 of 18 instances of dye-coupling involved horizontal cells, which are known to be electrically coupled. The close correspondence between all instances of dye-coupling observed in horizontal cells and the known electrophysiology of these cells suggests that in horizontal cells a single mechanism may be responsible for both processes, which is not unexpected since both involve the passage of ions from one cell to another.

In three different types of cells dye-coupling was demonstrated where electrical coupling had not been seen. Individual type I horizontal cells in the turtle retina were dye-coupled to a single type II horizontal cell a long distance away but it was not certain that these cells were electrically coupled. Furthermore, it was found that ganglion cells of the retina were frequently dye-coupled to each other (3 out of 4 cases). In a single Hermissenda ganglion, a cell 1 mm away from the injected cell, contacted by numerous processes of the injected cell, was dye-coupled to it.

EXAMPLE 4

Marking Cells

Cells were marked by passing constant-current hyperpolarizing pulses of one-second duration at a rate of one every two seconds. Since the dyes were negatively charged, they were ionophoresed from the electrode by applying a negative potential through a 10$^9$ ohm limiting resistor to the back of the micropipette.

Micropipettes were generally pulled from theta tubing manufactured from Corning 7740 glass. They were filled simply by injecting dye into the large end of the micropipette; filing was complete within a minute. When filled with a 5% solution of Lucifer Yellow CH, the micropipettes used to mark cells of the turtle retina had resistances between 500 and 200 M$\Omega$, those used to mark Hermissenda photoreceptors and hair cells had resistances of about 100 M$\Omega$, and those used to mark the large neurons of Hermissenda had resistances between 20 and 60 M$\Omega$. Cells were generally marked until the cell response began to deteriorate or, in the case of giant cells of Hermissenda, until a yellow color was visible under the dissecting microscope (usually 5–20 min). Turtle retinal cells were marked with 3 to 10 na, photoreceptors and hair cells of Hermissenda with 5 to 10 na, and the giant cells with 10 to 20 na.

Having thus described my invention, what I claim as new and desire to secure by Letters Patent is:

1. A compound represented by the following formula:

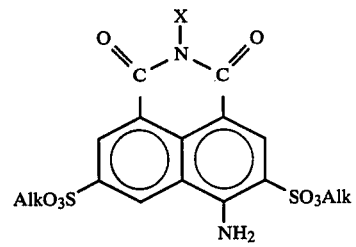

where
alk=alkali metal cation selected from Li$^+$, Na$^+$, K$^+$;
X=NH$_2$—NH—C(=O)—NH—,

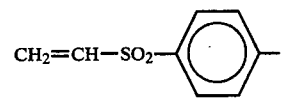

2. The compound of claim 1 wherein X=NH$_2$—NH—C(=O)—NH—.

3. The compound of claim 1 wherein X=
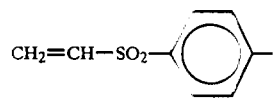
4. The compound of claims 1, 2, or 3 wherein alk=Li⁺.
* * * * *